United States Patent [19]

Kameyama

[11] 4,288,596
[45] Sep. 8, 1981

[54] FUROINDOLES

[75] Inventor: Tsutomu Kameyama, Nagoya, Japan

[73] Assignee: Taisho Pharmaceutical Co., Ltd., Tokyo, Japan

[21] Appl. No.: 82,728

[22] Filed: Oct. 9, 1979

[30] Foreign Application Priority Data

Mar. 31, 1978 [JP] Japan .................................. 53-37874

[51] Int. Cl.³ .......................................... C07D 491/048
[52] U.S. Cl. ................................ 546/198; 260/326.29; 424/267
[58] Field of Search ......................................... 546/198

[56] References Cited

U.S. PATENT DOCUMENTS

| 2,826,578 | 3/1958 | Perron | 544/400 X |
| 3,151,120 | 9/1964 | Werner | 546/198 |
| 3,312,739 | 4/1967 | Thomint | 544/400 X |
| 3,502,652 | 3/1970 | Jucker et al. | 544/400 X |
| 3,631,102 | 12/1971 | Narayanan | 544/400 X |

FOREIGN PATENT DOCUMENTS 54-130599 10/1979 Japan .

OTHER PUBLICATIONS

*Chemical Abstracts*, 89:109430d(1978), [Japan Kokai 78/34,798, 3/31/78, Kyogoku, et al.].

*Chemical Abstracts*, 86:72610X(1977), [Japan Kokai 76/63,194, 6/1/76, Yoshina, et al.].
*Chemical Abstracts*, 86:140014h(1977), [Japan Kokai 76/75,096, 6/29/76, Yoshina, et al.].
*Chemical Abstracts*, 87:68,329n(1977), [Japan Kokai 77/03,096,1/11/77, Yoshina, et al.].
*Chemical Abstracts*, 90:23017h(1979), [Japan Kokai 78/79,897,7/14/78, Kyogoku, et al.].
Rech, R., *J. Pharm Exp. Ther.*, 146,369(1965).

*Primary Examiner*—Richard A. Schwartz
*Attorney, Agent, or Firm*—George A. Loud

[57] ABSTRACT

The novel furoindole compounds of the formula

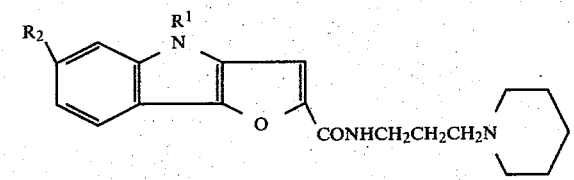

wherein $R^1$ is hydrogen or lower alkyl having 1–3 carbon atoms, and $R^2$ is hydrogen, halogen, trifluoromethyl, methoxy or methyl, are useful as analgesic and anti-inflammatory agents.

3 Claims, No Drawings

FUROINDOLES

BACKGROUND

Prior to the present invention, among the furoindoles, only furo[3,2-b]indole-2-(N,N-dimethyl)carboxamide compounds were known to have analgesic activity as described in *Chemical Abstracts*, 87, 68329r (1977) and ibid., 90, 23017h (1979).

The novel furoindole compounds of the present invention are distinguished from the known furoindoles by the absence of undesirable side-effects when using as analgesic and anti-inflammatory agents.

DESCRIPTION AND PREFERRED EMBODIMENTS

The present invention relates to a novel furoindole compound of the formula

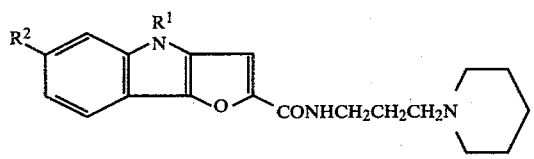

wherein $R^1$ is hydrogen or lower alkyl having 1–3 carbon atoms, and $R^2$ is hydrogen, halogen, trifluoromethyl, methoxy or methyl.

The object of the present invention is to provide novel furoindole compounds possessing excellent analgesic and antiinflammatory activity without undesirable side-effects.

In the present specification and claims, unless otherwise noted, the term "halogen" refers to chloro, bromo, iodo and fluoro.

A preferred compound of the present invention is the compound (I) wherein $R^1$ is methyl and $R^2$ is trifluoromethyl.

The compound (I) may be prepared, for example, by the following reaction sequence.

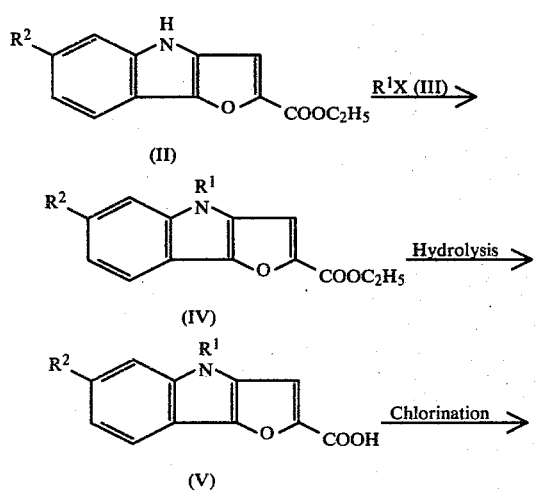

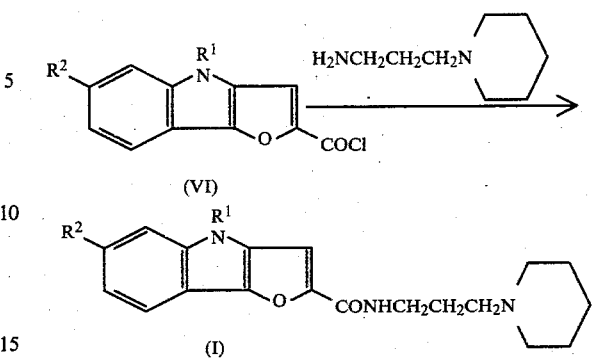

In this reaction sequence, $R^1$ and $R^2$ are same as defined above, and X is chloro, bromo or iodo. The reaction of the compound (II) with the compound (III) may be carried out in the presence of an alkali reagent such as sodium hydride, sodium methoxide or the like in an organic solvent such as dimethylformamide, ethyl ether, acetone or the like with stirring. The compound (IV) thus obtained may be hydrolyzed in a conventional manner to give the compound (V). The compound (V) may be treated with a chlorinating agent such as thionyl chloride to give the compound (VI). The compound (VI) may be allowed to react with N-(3-aminopropyl)-piperidine in a solvent such as benzene, acetone, chloroform, dichloromethane or the like. This reaction may be carried out with stirring for several hours at room temperature or on heating to about 90° C. When $R^1$ is hydrogen, the compound (II) is the same as the compound (IV), so the compound (II) may be directly allowed to hydrolyze to give the compound (V).

The compound (II) may be obtained by the method described in Japanese Patent Application Laying Open No. 125397/74 or ibid., 75096/76.

The compounds (I) of the present invention have excellent analgesic and anti-inflammatory activity without an undesirable side effect as compared with the known furoindoles as described above. That is, unlike the known furoindoles, the compounds of the present invention, when using as analgesic and anti-inflammatory agents, do not show side-effects such as psychotropic action. Furthermore, they show extremely low ulcerogenic action in stomach.

The following tests are illustrative of procedures of the biological assay for the compounds of the present invention, and the results are shown in Table 1. The compound Nos. in Table 1 are as defined in Examples as described hereinafter.

Test 1: ANALGESIC EFFECT BY ACETIC ACID WRITHING METHOD (Koster et al., *Fed Proc.*, 18, 412 (1959))

Ten mice of ddY strain weighing 18–24 g were used in testing each compound. Twenty minutes after oral administration of test compounds, 0.1 ml/10 g of 0.7% acetic acid solution was injected intraperitoneally and the number of writhing syndromes was recorded for 10 minutes from 10 minutes after acetic acid injection. $ED_{50}$ values were calculated from inhibition percent for each test compound.

Test 2: ANALGESIC EFFECT BY TAIL PRESSURE METHOD (Keijiro Takagi et al., Yakugaku Zasshi, 78, 553 (1941))

Ten mice of ddY strain weighing 18–24 g and showing pain threshold of 50–80 mmHg were used in testing each compound. The pain threshold was measured at 30, 60, 90 and 120 minutes after oral administration of the test compounds and positive analgesic response was recorded when the pain threshold was two or more times higher than pre-administration. $ED_{50}$ values were calculated from the numbers of positive mice.

Test 3: ANALGESIC EFFECT BY D'AMOUR-SMITH'S METHOD (D'Amour et al., J. Pharmacol. Exp. Ther., 72, 74 (1941))

Ten mice of ddY strain weighing 18–24 g and showing reaction times of 2–5 seconds were used in testing each compound. The reaction time was measured at 30, 60, 90 and 120 minutes after oral administration of the test compounds and positive analgesic response was recorded when the reaction time was two or more times longer than pre-administration. $ED_{50}$ values were calculated from the number of positive mice.

Test 4: ANTI-INFLAMMATORY EFFECT BY CARRAGEENIN EDEMA METHOD (Winter et al., Proc. Soc. Exp. Biol. Med., 111, 544 (1962))

Six male rats of Wistar strain weighing 110–120 g were used in testing each compound. The right hind paw of the rats was injected subcutaneously under the plantar surface with 0.1 ml of 1.0% carrageenin solution an hour after the oral administration of the test compounds, and foot volume was measured at 3 hours after carrageenin injection. $ED_{50}$ values were calculated from the inhibition percent of foot volume, and the ratios of anti-edematous action of test compounds were calculated by the formula; (the inhibition % of 100 mg/kg test compounds)/(the inhibition % of 100 mg/kg phenylbutazone).

Test 5: ULCERATION IN STOMACH (Brodie et al., Gastroenterology, 56, 206 (1969))

Ten male rats of Wistar strain weighing 190–200 g were used for each dose. Rats were deprived of food for 24 hours before experiments. Test compounds were administered orally and 18 hours later the rats were sacrificed, thereafter the area of each gastric lesion was measured and summed under dissecting microscope (×9). $UD_{50}$ values were calculated from the gastric lesion area.

TABLE 1

| Compound No. | Analgesic action ($ED_{50}$) mg/kg | | | Anti-inflammatory action ($ED_{50}$) mg/kg | Ulcerogenic action ($UD_{50}$) mg/kg |
|---|---|---|---|---|---|
| | Writhing method | Tail pressure method | D'Amour-Smith's method | | |
| 2 | 36.0 | 68.0 | 115.0 | 0.82* | |
| 5 | 64.2 | 80.0 | 100.0 | 0.73* | 400.0 |
| 6 | 29.5 | 50.0 | 59.0 | 1.29* | |
| 7 | 56.4 | 41.8 | 31.0 | 1.45* | |
| 8 | 68.4 | 87.0 | 100.0 | 0.56* | |
| 10 | 32.5 | 38.0 | 49.0 | 45.4 | —** |
| 11 | 30.0 | 41.0 | 50.0 | 1.29* | |
| 12 | 68.3 | 93.0 | 300.0 | 2.19* | 351.0 |
| 13 | 87.5 | 90.8 | 79.9 | 0.84* | |
| 14 | 81.2 | 84.6 | >100.0 | 0.92* | |
| 15 | 91.0 | 79.2 | 87.6 | 0.78* | |
| Aminopyrin | 38.0 | 98.0 | 225.0 | — | |
| Phenylbutazone | 123.0 | >300.0 | >300.0 | 110.0 | 145.0 |
| Ibuprofen | 195.0 | 324.0 | >300.0 | 66.5 | 278.0 |
| Tiaramide HCl | 66.0 | 110.0 | 93.0 | 84.3 | —** |

*Ratio of anti-edematous action; (100 mg/kg test compound)/(100 mg/kg phenylbutazone)
**Gastric lesion was scarcely observed up to 200 mg/kg For the use of the compounds of the present invention as analgesic and anti-inflammatory agents, these compounds may be administered orally in a conventional dosage form such as tablet, capsule or powder prepared according to conventional pharmaceutical practices. A single dose, or preferably, 2 to 4 divided daily doses, provided on a basis of about 1 to 10 mg/kg/day, is appropriate.

When six male rats of Wistar strain weighing 100–120 g were administered orally with 200 mg/kg of each compound of the present invention, no animals died for 7 days.

The following examples are illustrative of the present invention.

EXAMPLE 1

To ethyl furo[3,2-b]indole-2-carboxylate (10 g), 10% aqueous sodium hydroxide solution (100 ml) was added, then the mixture was stirred for an hour at 60° C. The resulting solution was acidified with hydrochloric acid, and the precipitate formed was collected by filtration to give furo[3,2-b]indole-2-carboxylic acid (8.5 g). To furo[3,2-b]-indole-2-carboxylic acid (8.5 g), thionyl chloride (40 ml) and benzene (50 ml) were added, the resulting solution was refluxed for 5 hours, and the excess amounts of thionyl chloride and the benzene were evaporated to give furo[3,2-b]indole-2-carbonyl chloride (7.1 g).

To a solution of furo[3,2-b]indole-2-carbonyl chloride (5 g) in benzene (100 ml), N-(3-aminopropyl)piperidine (6.5 g) in benzene (50 ml) was added dropwise, then the solution was stirred for 5 hours at room temperature. After filtration of the precipitate formed, the benzene was evaporated to give a crystalline product, which was recrystallized from benzene to give furo[3,2-b]indole-2-(N-piperidinopropyl)carboxamide (Compound No. 1) (5.5 g) melting at 198°–199° C.

EXAMPLE 2

To a suspension of sodium hydride (2.5 g) in dimethylformamide (100 ml), a solution of ethyl furo[3,2-b]indole-2-carboxylate (20 g) in dimethylformamide (100 ml) was added dropwise with stirring, then the mixture was stirred for 0.5 hour at room temperature. Methyl iodide (30 g) was added, and the resulting mixture was stirred for 5 hours at room temperature to give ethyl 4-methyl-furo[3,2-b]indole-2-carboxylate (18 g), which was hydrolyzed in a solution of sodium hydroxide (20 g) in water (200 ml) with stirring for an hour to give 4-methyl-furo[3,2-b]indole-2-carboxylic acid (15 g). This carboxylic acid was treated with thionyl chloride (50 ml) in benzene (70 ml) with stirring for an hour at 50° C. to give 4-methyl-furo[3,2-b]indole-2-carbonyl chloride (12 g).

To a solution of 4-methyl-furo[3,2-b]indole-2-carbonyl chloride (12 g) in benzene (200 ml), N-(3-aminopropyl)piperidine (14.6 g) in benzene (200 ml) was added dropwise with stirring, then the solution was stirred for 3 hours at room temperature. After filtration of the precipitate formed, the benzene was evaporated to give a crystalline product, which was recrystallized from petroleum benzine—benzine to give 4-methyl-furo[3,2-b]indole-2-(N-piperidinopropyl)carboxamide (Compound No. 2) (14 g) melting at 148°–150° C.

EXAMPLE 3

4-ethyl-furo[3,2-b]indole-2-carbonyl chloride (2.5 g) obtained according to the procedure as described in Example 2 using ethyl bromide instead of methyl iodide was dissolved in benzene (100 ml). To the solution, N-(3-aminopropyl)piperidine (3 g) in benzene (50 ml) was added dropwise with stirring, then the solution was stirred for 2.5 hours at room temperature. After filtration of the precipitate formed, the benzene was evaporated to give a crystalline product, which was recrystallized from petroleum benzine—benzene to give 4-ethyl-furo[3,2-b]indole-2-(N-piperidinopropyl)carboxamide (Compound No. 3) (2.7 g) melting at 127°–129° C.

EXAMPLE 4

4-isopropyl-furo[3,2-b]indole-2-carbonyl chloride (2 g) obtained according to the procedure as described in Example 2 using isopropyl bromide instead of methyl iodide was dissolved in benzene (100 ml). To this solution, N-(3-aminopropyl)piperidine (2.5 g) in benzene (50 ml) was added dropwise with stirring, then the solution was stirred for 2.5 hours at room temperature. After filtration of the precipitate formed, the benzene was evaporated to give a crystalline product, which was recrystallized from n-hexane—benzene to give 4-isopropyl-furo[3,2-b]indole-2-(N-piperidinopropyl)—carboxamide (Compound No. 4) (2.4 g) melting at 131°–132° C.

EXAMPLE 5

Following the hydrolysis as described in Example 1 using ethyl 6-chloro-furo[3,2-b]indole-2-carboxylate instead of ethyl furo[3,2-b]indole-2-carboxylate, there was obtained 6-chloro-furo[3,2-b]indole-2-carboxylic acid, which was treated with thionyl chloride according to the procedure as described in Example 1 to give 6-chloro-furo[3,2-b]indole-2-carbonyl chloride.

6-chloro-furo[3,2-b]indole-2-carbonyl chloride (5 g) was allowed to reacted with N-(3-aminopropyl)piperidine (6.5 g) according to the procedure as described in Example 1, and the precipitate formed was recrystallized from ethanol to give 6-chloro-furo[3,2-b]indole-2-(N-piperidinopropyl)carboxamide. (Compound No. 5) (6.2 g) melting at 232°–233° C.

EXAMPLE 6

Following the procedure as described in Example 2 using ethyl 6-chloro-furo[3,2-b]indole-2-carboxylate and methyl iodide, there was obtained 6-chloro-4-methyl-furo[3,2-b]indole-2-carbonyl chloride. To a solution of 6-chloro-4-methyl-furo[3,2-b]indole-2-carbonyl chloride (2.68 g) in benzene (100 ml), a solution of N-(3-aminopropyl)piperidine (3.0 g) in benzene (50 ml) was added dropwise with stirring, then the resulting solution was stirred for 3 hours at room temperature. After filtration of the precipitate formed, the benzene was evaporated to give a crystalline product, which was recrystallized from petroleum benzine—benzene to give 6-chloro-4-methyl-furo[3,2-b]indole-2-(N-piperidinopropyl)carboxamide (Compound No. 6) (3.18 g) melting at 154°–156° C.

EXAMPLE 7

Following the procedure as described in Example 6 using ethyl iodide instead of methyl iodide, there was obtained 6-chloro-4-ethyl-furo[3,2-b]indole-2-carbonyl chloride.

To a solution of 6-chloro-4-ethyl-furo[3,2-b]indole-2-carbonyl chloride (2.8 g) in benzene (100 ml), N-(3-aminopropyl)piperidine (2.8 g) in benzene (50 ml) was added dropwise with stirring, then the solution was stirred for 2 hours at room temperature. After filtration of the precipitate formed, the benzene was evaporated to give a crystalline product, which was recrystallized from n-hexane—acetone to give 6-chloro-4-ethyl-furo[3,2-b]indole-2-(N-piperidinopropyl)carboxamide (Compound No. 7) (3.1 g) melting at 137°–138° C.

EXAMPLE 8

Following the procedure as described in Example 6 using isopropyl bromide instead of methyl iodide, there was obtained 6-chloro-4-isopropyl-furo[3,2-b]indole-2-carbonyl chloride.

To a solution of 6-chloro-4-isopropyl-furo[3,2-b]indole-2-carbonyl chloride (3 g) in benzene (100 ml), N-(3-aminopropyl)piperidine (2.9 g) in benzene (50 ml) was added dropwise, then the solution was refluxed for an hour. After filtration of the precipitate formed, the benzene was evaporated to give a crystalline product, which was recrystallized from petroleum benzine—benzene to give 6-chloro-4-isopropyl-furo[3,2-b]indole-2-(N-piperidinopropyl)carboxamide (Compound No. 8) (3.2 g) melting at 141°–142° C.

EXAMPLE 9

Following the hydrolysis as described in Example 1 using ethyl 6-trifluoromethyl-furo[3,2-b]indole-2-carboxylate (10 g) instead of furo[3,2-b]indole-2-carboxylic acid, there was obtained 6-trifluoromethyl-furo[3,2-b]indole-2-carboxylic acid (8.5 g), which was treated with thionyl chloride to give 6-trifluoromethyl-furo[3,2-b]indole-2-carbonyl chloride (7.8 g). This carbonyl chloride (5 g) was allowed to react with N-(3-aminopropyl)piperidine (6.5 g) according to the procedure described in Example 1, and the precipitate formed was recrystallized from benzene to give 6-trifluoromethyl-furo[3,2-b]indole-2-(N-piperidinopropyl)-carboxamide (Compound No. 9) (5.5 g) melting at 198°–199° C.

EXAMPLE 10

Following the procedure as described in Example 2 using ethyl 6-trifluoromethyl-furo[3,2-b]indole-2-carboxylate and methyl iodide, there was obtained 6-trifluoromethyl-4-methyl-furo[3,2-b]indole-2-carbonyl chloride.

To a solution of 6-trifluoromethyl-4-methyl-furo[3,2-b]indole-2-carbonyl chloride (3.8 g) in benzene (50 ml), N-(3-aminopropyl)piperidine (4 g) in benzene (200 ml) was added dropwise, then the solution was stirred for 2 hours at room temperature. After evaporation of the benzene, the residue was extracted with methylene chloride and dried over anhydrous sodium sulfate. Evaporation of the methylene chloride left a crystalline product, which was recrystallized from n-hexane—acetone to give 4-methyl-6-trifluoromethyl-furo[3,2-b]indole-2-(N-piperidinopropyl)carboxamide (Compound No. 10) (4.1 g) melting at 155°–156° C.

EXAMPLE 11

Following the procedure as described in Example 10 using ethyl bromide instead of methyl iodide, there was obtained 4-ethyl-6-trifluoromethyl-furo[3,2-b]-indole-2-carbonyl chloride.

To a solution of 4-ethyl-6-trifluoromethyl-furo[3,2-b]-indole-2-carbonyl chloride (3.2 g) in benzene (50 ml), N-(3-aminopropyl)piperidine (2.9 g) in benzene (200 ml) was added dropwise, then the solution was stirred for 2 hours at room temperature. After evaporation of the benzene, the residue was recrystallized from n-hexane-—acetone to give 4-ethyl-6-trifluoromethyl-furo[3,2-b]indole-2-(N-piperidinopropyl)carboxamide (Compound No. 11) (3.5 g) melting at 124°–126° C.

EXAMPLE 12

Following the procedure as described in Example 10 using isopropyl bromide instead of methyl iodide, there was obtained 4-isopropyl-6-trifluoromethyl-furo[3,2-b]indole-2-carbonyl chloride.

To a solution of 4-isopropyl-6-trifluoromethyl-furo[3,2-b]indole-2-carbonyl chloride (3.3 g) in benzene (50 ml), N-(3-aminopropyl)piperidine (2.8 g) in benzene (200 ml) was added dropwise, then the solution was stirred for 2 hours at room temperature. After evaporation of the benzene, the residue was extracted with methylene chloride and dried over anhydrous sodium sulfate. Evaporation of the methylene chloride left a crystalline product, which was recrystallized from n-hexane—acetone to give 4-isopropyl-6-trifluoromethyl-furo[3,2-b]indole-2-(N-piperidinopropyl)carbonxamide (Compound No. 12) (13.5 g) melting at 128°–129° C.

EXAMPLE 13

Following the procedure as described in Example 2 using ethyl 6-fluoro-furo[3,2-b]indole-2-carboxylate and ethyl bromide instead of ethyl furo[3,2-b]indole-2-carboxylate and methyl iodide, respectively, there was obtained 4-ethyl-6-fluoro-furo[3,2-b]indole-2-carbonyl chloride.

To a solution of 4-ethyl-6-fluoro-furo[3,2-b]indole-2-carbonyl chloride (12 g) in benzene (200 ml), N-(3-aminopropyl)piperidine (15 g) in benzene (200 ml) was added dropwise with stirring, then the solution was stirred for 3 hours at room temperature. After filtration of the precipitate formed, the benzene was evaporated to give a crystalline product, which was recrystallized from petroleum benzine—benzene to give 4-ethyl-6-fluoro-furo[3,2-b]indole-2-(N-piperidinopropyl)carboxamide (Compound No. 13) (13 g) melting at 132°–133° C.

EXAMPLE 14

Following the procedure as described in Example 2 using ethyl 6-methoxy-furo[3,2-b]indole-2-carboxylate and n-propyl bromide instead of ethyl furo[3,2-b]indole-2-carboxylate and methyl iodide, respectively, there was obtained 6-methoxy-4-n-propyl-furo[3,2-b]indole-2-carbonyl chloride.

To a solution of 6-methoxy-4-n-propyl-furo[3,2-b]-indole-2-carbonyl chloride (12 g) in benzene (200 ml), N-(3-aminopropyl)piperidine (15 g) in benzene (200 ml) was added dropwise with stirring, then the solution was stirred for 3 hours at room temperature. After filtration of the precipitate formed, the benzene was evaporated to give a crystalline product, which was recrystallized from petroleum benzine—benzene to give 6-methoxy-4-n-propyl-furo[3,2-b]-indole-2-(N-piperidinopropyl)carboxamide (Compound No. 14) (12 g) melting at 195°–196° C.

EXAMPLE 15

Following the procedure as described in Example 2 using ethyl 6-methyl furo[3,2-b]indole-2-carboxylate and n-propyl bromide instead of ethyl furo[3,2-b]indole-2-carboxylate and methyl iodide, respectively, there was obtained 6-methyl-4-n-propyl-furo[3,2-b]indole-2-carbonyl chloride.

To a solution of 6-methyl-4-n-propyl-furo[3,2-b]indole-2-carbonyl chloride (12 g) in benzene (200 ml), N-(3-aminopropyl)piperidine (15 g) in benzene (200 ml) was added dropwise with stirring, then the solution was stirred for 3 hours at room temperature. After filtration of the precipitates which formed, the benzene was evaporated to give a crystalline product, which product was recrystallized from petroleum benzine—benzene to give 6-methyl-4-n-propyl-furo[3,2-b]indole-2-(N-piperidinopropyl)carboxamide (Compound No. 15) (11 g) melting at 130°–132° C.

What is claimed is:

1. A furoindole compound of the formula

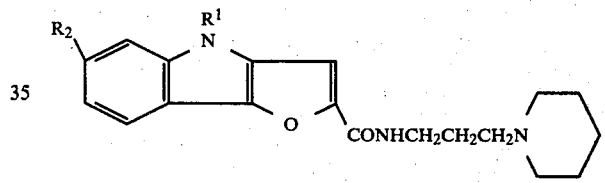

wherein $R^1$ is hydrogen or lower alkyl having 1–3 carbon atoms, and $R^2$ is hydrogen, trifluoromethyl, methoxy or methyl.

2. A furoindole compound of the formula:

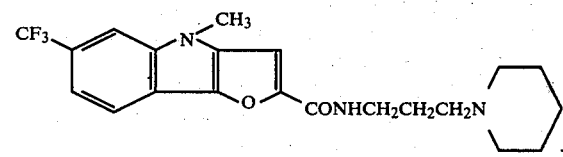

3. A furoindole compound of the formula

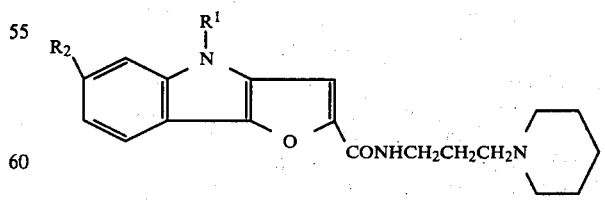

wherein $R^1$ is hydrogen, ethyl or isopropyl and $R^2$ is hydrogen or trifluoromethyl.

* * * * *

UNITED STATES PATENT AND TRADEMARK OFFICE
CERTIFICATE OF CORRECTION

PATENT NO. : 4,288,596
DATED : 8 September 1981
INVENTOR(S) : Tsutomu Kameyama

It is certified that error appears in the above—identified patent and that said Letters Patent is hereby corrected as shown below:

Col. 3, line 64 (Table I, second column, 7th number in column) "30.0" should read ---50.0---.

Col. 4, line 11, after "compound" insert ---)---.

Col. 5, line 49, "reacted" should read ---react---.

Col. 7, line 34, "carbonxamide" should read ---carboxamide---;

line 35, "13.5 g" should read ---3.5g---.

Signed and Sealed this

Twenty-second Day of December 1981

|SEAL|

Attest:

GERALD J. MOSSINGHOFF

Attesting Officer      Commissioner of Patents and Trademarks